United States Patent [19]

Brazhnikov et al.

[11] 4,414,857
[45] Nov. 15, 1983

[54] METHOD AND APPARATUS FOR INJECTING SAMPLES INTO GAS CHROMATOGRAPH

[76] Inventors: Vadim V. Brazhnikov, ulitsa 26 Bakinskikh komissarov, 3, korpus 3, kv. 324; Eduard P. Skornyakov, Kronshtadsky bulvar, 49, kv. 66; Jury A. Sultanovich, Profsojuznaya ulitsa, 3, korpus 3, kv. 53; Vladimir M. Poshemansky, 2 Pavlovsky pereulok, 20, kv. 80; Karl I. Sakodynsky, ulitsa Vavilova, 12, kv. 29; Semen S. Berlin, ulitsa Sovkhoznaya, 53, korpus 1, kv. 33; Vladimir V. Ogurtsov, Fergansky proezd, 14, korpus 2, kv. 81; Vladimir V. Alekhin, ulitsa Kuusinena, 6, korpus 7, kv. 79, all of Moscow, U.S.S.R.

[21] Appl. No.: 291,390

[22] Filed: Aug. 10, 1981

[30] Foreign Application Priority Data

Aug. 16, 1979 [SU] U.S.S.R. .................................. 2808727

[51] Int. Cl.³ .......................................... G01N 31/08
[52] U.S. Cl. ............................ 73/863.11; 73/864.87
[58] Field of Search ........... 73/863.11, 863.12, 864.85, 73/864.86, 864.87, 864.84, 23.1

[56] References Cited

U.S. PATENT DOCUMENTS

| | | | |
|---|---|---|---|
| 2,839,152 | 6/1958 | Tracht | 73/23.1 |
| 3,247,704 | 4/1966 | Konig | 73/23.1 |
| 3,566,698 | 3/1971 | Sheppard | 73/864.85 |
| 3,889,538 | 6/1975 | Fingerle | 73/863.11 |
| 3,985,016 | 10/1976 | Haruki | 73/864.86 |

*Primary Examiner*—S. Clement Swisher
*Attorney, Agent, or Firm*—Steinberg & Raskin

[57] ABSTRACT

Disclosed is a method and apparatus for injecting samples into the evaporator of a gas chromatograph effected by a sample carrier, whereafter the thus formed vapors are transferred into the flow of a carrier gas. According to one aspect of the invention, the evaporator of the gas chromatograph is sealed only for a period of the sample introduction subsequent to the physical communication of the evaporator with the sample carrier. Vapors of the substance under analysis are conveyed from the evaporator into the chromatographic column via a flow constrictor of constant cross-sectional diameter.

According to another aspect of the invention the flow constrictor of constant cross-section is positioned essentially after the passageway communicating the sample carrier with the evaporator but prior to the passageway for evacuating the vapors from the evaporator to the chromatographic column. The sample carrier is provided with a sealing element for sealingly blocking the passageway communicating the sample carrier with the evaporator during sample injection.

15 Claims, 10 Drawing Figures

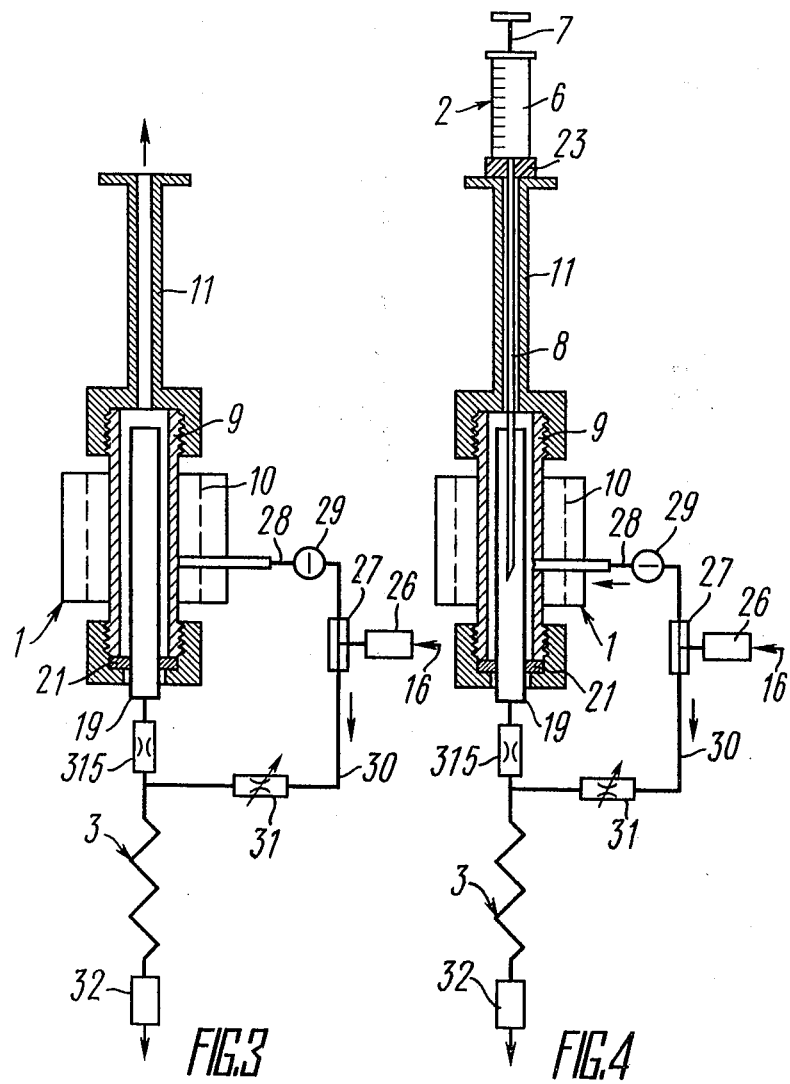

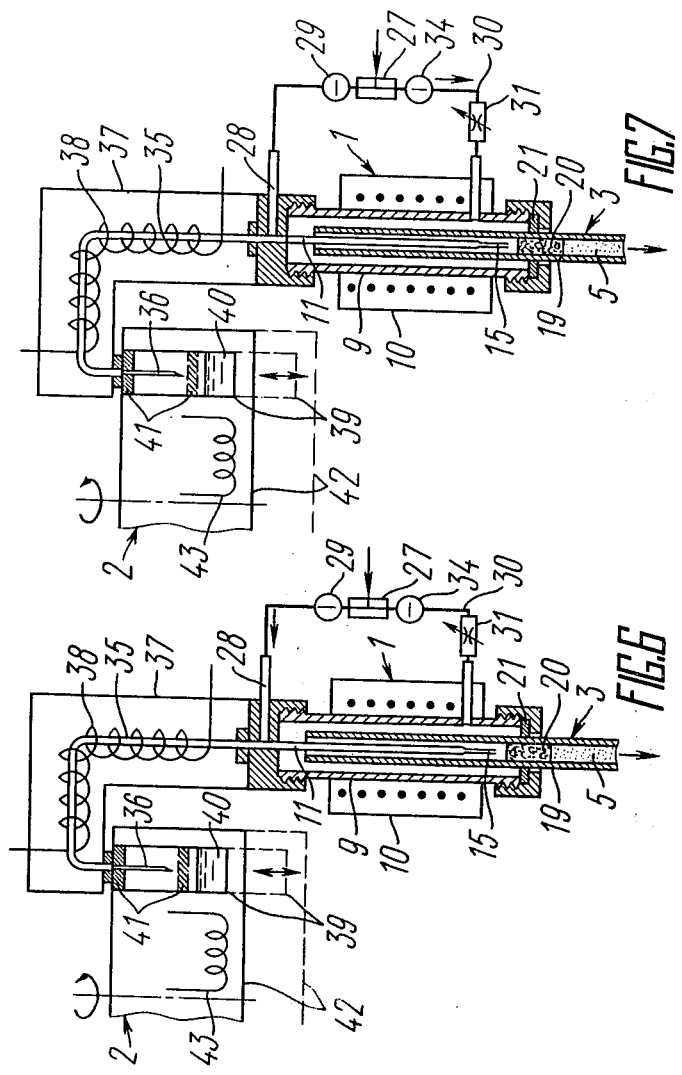

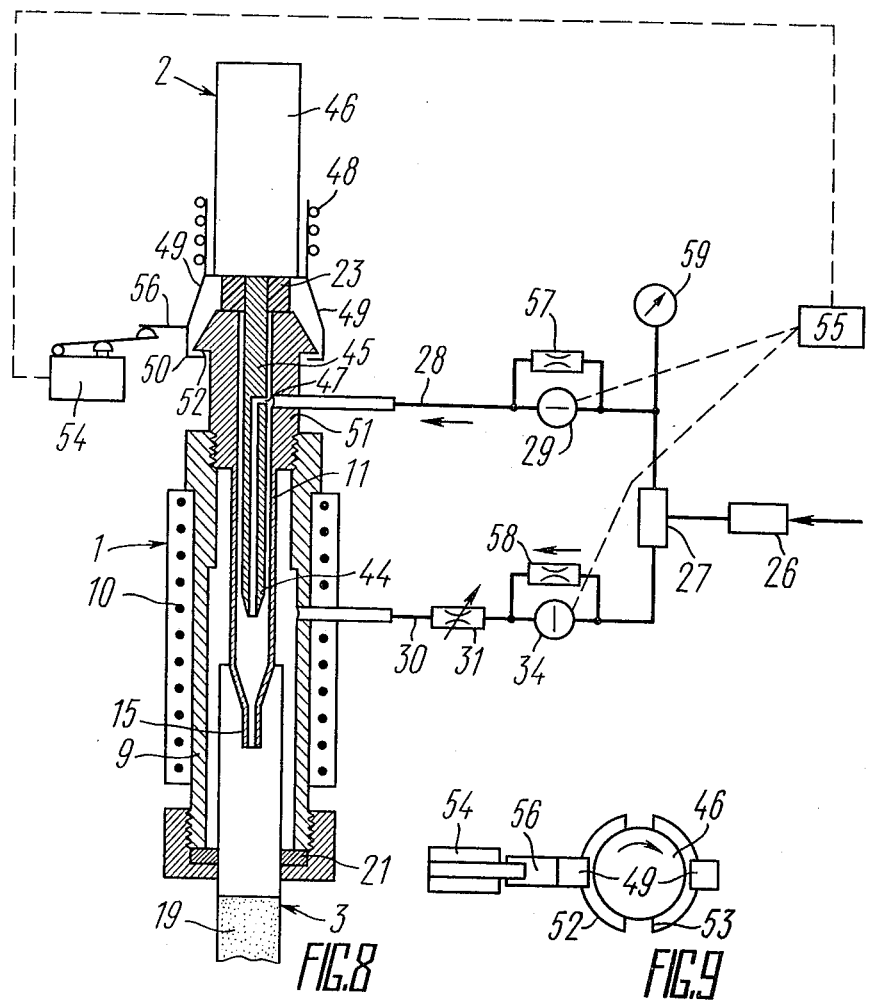

METHOD AND APPARATUS FOR INJECTING SAMPLES INTO GAS CHROMATOGRAPH

FIELD OF THE INVENTION

The present invention relates to gas chromatography, and more particularly to a method and means for introducing samples into gas chromatographs. The invention can find application in analyzing trace contaminants of solid, gaseous and liquid mixtures of organic and inorganic compounds.

BACKGROUND OF THE INVENTION

Known in the art is a method of syringing samples into the pressure-sealed evaporator of a gas chromatograph continuously blown through by a flow of inert carrier gas. The sample is introduced by piercing by a syringe needle septums of self-sealing material sealingly blocking the inlet ports of the evaporators and thus injecting a liquid sample into the interior volume thereof. The sample vapours formed in the interior volume of the evaporator are carried by the carrier gas to the chromatographic column.

Accuracy of the chromatographic analyses made by practically all heretofore known gas chromatographs employing a sample injecting syringe is seriously affected by the use of a septum of self-sealing material, such as silicone rubber, closing or blocking the inlet port of the evaporator to be pierced by the syringe needle. There are two major problems encountered in conjunction with the use of self-sealing septums: contamination of the chromatographic system by the material of the septum interfering with the analysis in a sensitive instrument during temperature programming, and the loss of self-sealing capacity of the septum after several, usually 10 to 20, punctures made by the syringe needle. The septum generally causes "ghost peaks" recorded in the chromatogram in the course of temperature programming of the column even without a sample being introduced. There are at least four reasons for such contamination: release of gaseous substances by the septum under the action of high temperatures developed in the evaporator; exhaust of volatile components of the pieces of the septum broken away therefrom, entrapped by the syringe needle and introduced into the evaporator together with the sample; residues of the previous sample absorbed by the septum due to reverse diffusion of the volatile substances in the evaporator; and residues of the previous samples accumulated in the course of the septum material reacting with the sample in the syringe needle.

From 1967 onwards a number of inventions have been patented in various countries directed to prevent the above factors from interfering with the accuracy of the chromatographic measurements. Among the very first such inventions was the one exemplified by U.S. Pat. No. 3,581,573, published in 1971, contemplating the use of a septum shield in the form of a strip of inert material, such as polytetrafluoroethylene, arranged to overlie the face of the septum exposed to the interior of the evaporator and intended to be shifted or displaced after each piercing of the septum and the shield.

Another invention is known to have been patented in 1972 and disclosed in U.S. Pat. No. 3,635,093, which teaches that interposed slidingly between the septum and the interior of the evaporator is a metal shield with an opening therein, the opening being put into registration with the inlet port of the head portion of the evaporator prior to piercing the septum with the syringe needle and then moved out of registration with the septum puncture for the septum to be completely insulated from the heated area of the evaporator.

Another invention intended to prevent the septum from interfering with the results of chromatographic analysis is disclosed in U.S. Pat. No. 3,939,713, published in 1976. The remedial feature of this invention resides in that the septum is totally shielded from the interior volume of the evaporator by turning the evaporator head, subsequent to each sample injection.

However, the heretofore cited inventions offer but partial solution to the septum problem. While preventing contamination caused by the volatile substances of the septum, they fail to eliminate the penetration of, for example, parts of the septum material introduced into the evaporator by the syringe needle. In addition, other problems, such as pressure-tightness of the septum etc., have not been completely resolved.

To alleviate the disadvantages connected with the use of self-sealing septums, a novel system have been developed for introducing samples enclosed by sealed capsules of inert metal, such as aluminum, gold and the like. The capsule is introduced through an inlet port into the evaporator to be punctured or pierced by a hollow needle, whereafter the capsule content is "rinsed" by the flow of heated transfer gas and conveyed to the chromatographic column (cf. U.S. Pat. No. 3,783,794, published in 1974).

Inherent in this system is its structural complexity due to an excessive number of moving elements subjected to friction.

In more recent years a method of introducing samples into a gas chromatograph has been proposed, whereby a liquid sample is injected into the evaporator of a gas chromatograph through the inlet port thereof provided with and sealed by a rotatable shut-off valve. Prior to inserting a syringe needle into the evaporator, the latter is depressurized; after a sample has been injected and the needle removed from the evaporator, the inlet port is again sealingly closed by means of said rotatable valve.

The system suffers from a disadvantage residing in that the rotatable valve is located in the immediate proximity to the heated area of the evaporator; the valve being intended to ensure a sealing closure of the inlet port of the evaporator without lubrication, by virtue of high accuracy mating of the polished surfaces thereof alone. This affects adversely the reliability of the gas chromatograph, especially when analyzing substances with high boiling point, such as in excess of 450° C. Another disadvantage is in that only a syringe must be employed as the sample carrier, which limits the range of substances that can be thus subjected to analysis, since only liquid or gaseous substances can be introduced by means of a hypodermic syringe (cf. K. Grob and K. Grob Jr. "Journal of Chromatography" No. 151, p. 311, 1978).

SUMMARY OF THE INVENTION

It is an object of the present invention to provide such a method for introducing samples into a gas chromatograph which to a considerable extent would eliminate the penetration of contaminants into the sample vapours thereby attaining more accurate and reliable results of chromatographic measurements.

Another object of the invention is the provision of an apparatus for introducing samples into a gas chromatograph of simple and reliable construction featuring no movable elements operable in the high temperature zone of the evaporator.

Among other objects are to eliminate structural elements capable of introducing contaminants into the vapours under analysis and to expand the range of substances being analyzed, as well as their phases, viz. liquid, gaseous and solid phases.

This is attained by that in a method of introducing samples of substances under analysis by means of a sample probe or carrier into the evaporator of a gas chromatograph for a consequent transfer of the vapours of such substances by a flow of a carrier gas into a chromatographic column of the gas chromatograph, according to the invention, the evaporator of the gas chromatograph is sealed only during injection of the sample after physically communicating the evaporator with the sample carrier, the vapours of the substances under analysis being transferred from the evaporator into the chromatographic column via a flow constrictor of constant cross-section, the evaporator being communicated with the atmosphere subsequent to such a transfer.

The method is advantageous in that by virtue of sealing the evaporator exclusively for the sample injection and communicating the evaporator with the atmosphere subsequent to the transfer of vapours through the flow constrictor of constant cross-section into the chromatographic column, no foreign substances enter the chromatographic column from the evaporator during the chromatographic analysis of the thus introduced sample until a subsequent sample is introduced thereinto, while the interior volume of the evaporator is backflushed or blown off by a portion of the carrier gas flow entering the inlet port of the column. This helps to prevent contaminants from penetrating the injected sample and ensures more reliable and accurate results of the chromatographic analysis to be obtained.

In a simple version of effecting the method according to the invention, the liquid sample is injected into the evaporator by means of a sample probe or carrier, such as a hypodermic syringe, the physical volume of the portion thereof inserted into the evaporator, for example a needle thereof, is somewhat less than or approximates to the interior volume of the evaporator. The liquid sample introduced into the evaporator is caused to vaporize and sharply increase its volume, thereby creating a vapor overpressure inside the evaporator which is sufficient for transferring the sample from the evaporator via the flow constrictor into the flow of carrier gas entering the chromatographic column.

Preferably, the substance under analysis is conveyed from the evaporator into the chromatographic column by the flow of carrier gas supplied to the evaporator after it has been sealed. Therewith, following the transfer of the vapours from the evaporator into the chromatographic column, the flow of carrier gas supplied to the evaporator is cut-off and this flow is then directed to the inlet port of the chromatographic column downstream of the flow constrictor.

The present invention further provides an apparatus for effecting the method according to the invention, wherein the sample carrier is adapted to periodically communicate with the evaporator having a passageway for communicating the sample carrier with the evaporator, a conduit for feeding the carrier gas to the evaporator, and a passageway for conveying the vapours of substances under analysis from the evaporator to the chromatographic column. According to another feature of the invention, arranged between the passageway communicating the sample carrier with the evaporator and the passageway for conveying the vapours of substances under analysis from the evaporator to the chromatographic column is a flow constrictor of constant cross-section, while the sample carrier is provided with a sealing element for sealingly engaging the sample carrier with the evaporator during sample injection.

A major advantage of this apparatus for injecting samples resides in that it makes no use of a self-sealing septum, which prevents contaminants and volatile substances of the septum from penetrating into the sample material to thereby improve the reliability and accuracy of the chromatographic analysis. In contrast to the prior art appratuses, the sample injector according to the invention is free from any movable highly polished elements, such as gate valves, slide valves, etc., ordinarily disposable in close proximity to the heated area of the evaporator. This in turn improves the reliability of the apparatus, especially when operated under high temperatures (in excess of 400° C.) developed in the evaporator. Also, the present apparatus makes it possible to use various known types of sample carriers, such as syringes, pipettes, ampules, etc., which provides for a wider range of sample substances introduceable by means of the herein proposed device.

A less complicated modification of the arrangement according to the invention to be employed in conjunction with any known conventional gas chromatograph without redesigning it structurally provides for the use of a flow constrictor of constant cross-section disposed inside the evaporator and having the form of a capillary tube extending the passageway communicating the sample carrier with the evaporator.

In another modified form of the sample injection arrangement, the flow constrictor of constant cross-section is located at the outlet from the evaporator to be integral with the passageway for evacuating the vapours of substances under analysis from the evaporator into the chromatographic column. This modification is especially advantageous for use in conjunction with temperature programmable chromatographic columns. The flow constrictor is preferably disposed in the column oven.

One more embodiment of the sample injection arrangement provides for employment of the flow constrictor or restrictor in the form of a tube filled with particulate sorbent. The sorbent may be the same as that used in the chromatographic column. This modification is preferably used in conjunction with gas chromatographs provided with means for backwashing or blowing off the heavy sample components in order to speed up the chromatographic analysis of the light components.

A preferred embodiment of the apparatus includes a flow divider installed in the carrier gas supply pipe, one outlet line of the divider communicating with the passageway for evacuating the sample vapours from the evaporator into the chromatographic column upstream of the flow constrictor, the outlet line being provided with a shut-off valve. Another outlet line of the flow divider communicates with the passageway for evacuating the sample vapours from the evaporator into the chromatographic column downstream of the flow constrictor and is provided with an adjustable flow constrictor. This arrangement is intended for the carrier gas to entrain the substances under analysis and carry them from the evaporator into the chromatographic column, whereby reproducibility of sample injection is increased.

Further, this embodiment may be provided with an additional controllable shut-off valve to be positioned in the outlet line from the flow divider having the adjustable flow constrictor.

To inject samples of vapour phase thermodynamically balanced with the liquid or solid substance under analysis, a still further modification of the apparatus is envisaged, wherein a hollow elongated needle with a pointed or sharp end extending from the evaporator serves as the passageway for communicating the sample carrier with the evaporator. The sample carrier is generally an ampoule partially filled with a substance under analysis, the upper portion or neck thereof being blocked by a septum or membrane of self-sealing material. The ampoule is adapted to be displaced toward the pointed needle end such that at the moment of vapour phase sample introduction begins by the needle being caused to pierce the self-sealing septum thereby communicating the interior volume of the ampoule with the evaporator. In order to prevent the vapours from condensing, the hollow needle is preferably enclosed into a temperature-controlled housing with the pointed end of the needle extending therefrom.

For improved operational reliability during the introduction of measured quantities of liquid samples, the sample carrier may have the form of a capillary tube having a hermetically closed end thereof attached to a holder, the capillary tube having a lateral bore or drilling adjacent to the closed portion. The capillary tube is also provided with a sealing sleeve of inert deformable material. This construction is especially advantageous for introducing small quantities of liquid sample (up to 1 microliter), since it prevents fractionation of sample constituents.

Improved reliability of the apparatus is attained in the construction heretofore described by that the capillary holder is provided with spring-biased clamps having the form of flexible plates with crimped hook-like ends. The head portion of the evaporator has a collar to lockingly engage with the crimped ends of said plates, the head collar being tapered outwardly, the tapered portion of the head collar being provided with grooves extending longitudinally or axially therealong. Further, to automate the sample injection operation, an electrical microswitch is arranged in close proximity to the evaporator head. The construction also includes a control unit for controlling the shut-off valves, the control unit being electrically connected with the microswitch, while one of the plates of the spring-biased clamps has a rib cooperating with said microswitch at the point of operation when the passageway is sealed prior to communicating the sample carrier with the evaporator.

Alternatively, to provide for the introduction of solid substance samples, the sample carrier may have the form of a rod-like member from ferromagnetic material, whereas the body of the evaporator may be encompassed by an induction coil.

BRIEF DESCRIPTION OF THE DRAWINGS

The invention will now be described in greater detail with reference to specific embodiments thereof taken in conjunction with the accompanying drawings, in which:

FIG. 3 shows another embodiment of the sample injection arrangement illustrating a point of operation thereof immediately preceding sample introduction, the embodiment providing for the division of the carrier gas flow;

FIG. 4 shows the apparatus of FIG. 3 with a sample carrier inserted thereinto;

FIG. 6 shows, in part schematically and in part sectionally, an embodiment of the apparatus according to the invention intended for introducing a vapour phase in equilibrium with the liquid or solid phase at the moment immediately preceding sample introduction;

FIG. 7 shows the apparatus of FIG. 6 at the point of introducing the vapour phase;

FIG. 8 illustrates an embodiment of the apparatus according to the invention with a sample carrier of the pipette type;

FIG. 9 is a partial top plan view of FIG. 8; and

BEST MODE OF CARRYING OUT THE INVENTION

Disclosed hereinbelow are various embodiments of a sample injection arrangement according to the invention. The method according to the invention will become more fully apparent from the consideration of the constructions and modes of operation of the arrangement.

Figure 1:
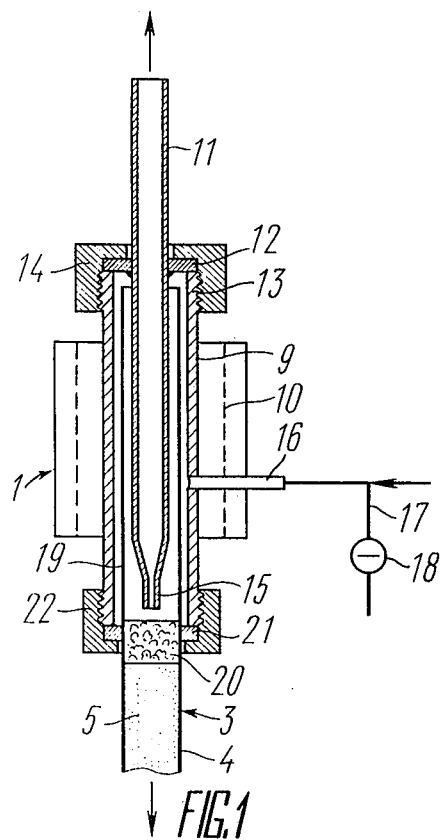
FIG. 1 is a sectional view of a simple form of a sample injection arrangement according to the invention at the moment immediately preceding sample introduction, the chromatographic column being shown in part.
Figure 2:
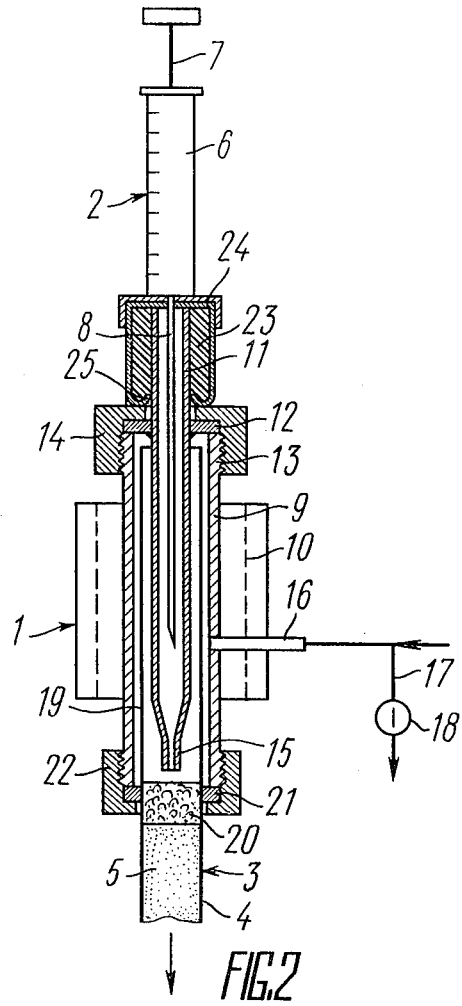
FIG. 2 shows the apparatus of FIG. 1 with a sample carrier inserted thereinto.

With reference to FIGS. 1 and 2, there is shown a less complicated preferred embodiment of the sample injector in two operating positions, viz., prior to injecting a sample (FIG. 1) and during the injection (FIG. 2). Indicated generally by numerals 1, 2 and 3 are evaporator, sample carrier and chromatographic column, respectively. The chromatographic column 3 can be of any known suitable construction and has the form of a tube 4 of inert material, such as glass, filled with particulate sorbent 5. The sample carrier 2, which is integral with the sample injection arrangement, can also be of any known conventional design and in this modification represents generally a syringe having a body 6 made from transparent material, such as glass, the internal passage thereof being provided with a mandrin 7 capable of longitudinal displacement along the axial passage of the syringe. Communicating with the body 6 of the syringe is a hollow needle 8, the inner passage of which is in fact an extension of the internal passage of the body 6.

Arranged integrally with the herein proposed sample injector, the evaporator 1 is comprised of a cylindrical body 9 made from inert heat-resistant material, such as stainless steel, and a heater 10. Disposed inside the body 9 of the evaporator 1 is a tubular element 11 defining a passageway or channel to communicate the sample carrier 2 with the evaporator 1. In the presently disclosed embodiment, communication between the sample carrier 2 and the evaporator 1 is effected by inserting the hollow needle 8 of the hypodermic syringe into the interior volume of the tubular element 11, the size of the tube 11 being selected such that the interior volume of the needle 8 would approximate the interior volume of the tube 11, but be somewhat less than the latter for the needle 8 to be positioned with a minimum clearance relative to the inside walls of the tube 11. The tube 11 is provided with a sealing ring 12 of soft metal, such as aluminum or copper, which is pressed for sealing engagement against a head 13 of the body 9 of the evaporator 1 by a coupling nut 14. The sealing ring 12 is joined with the tube 11 such as by welding. Accommodated inside the evaporator 1 is a flow constrictor 15 of a preset or constant cross-section in the form of a capillary tube extending from the tubular element 11. Arranged to communicate with the evaporator 1 is a conduit 16 serving to feed the evaporator with an inert carrier gas, such as nitrogen. The conduit 16 is provided with a by-pass pipe 17 having a controllable shut-off valve 18, such as an electromagnetically controlled valve. Located in the interior of the evaporator 1 in an annular gap formed between the walls of the body 9 and the tubular element 11 is a tube 19 defining a passageway for evacuating the vapours of substances being analyzed from the evaporator 1 into the chromatographic column 3. In the embodiment illustrated in FIGS. 1 and 2 the chromatographic column 3 is in fact an extension of the passageway for evacuating the vapours from the evaporator 1 and is separated therefrom by a filter 20 of inert fibrous material such as glass fiber. Pressure-tightness of the location where the tube 19 extends away from the evaporator 1 is ensured by the provision of a sealing element 21 pressed for sealing engagement against the end surface of the cylindrical body 9 of the evaporator 1 facing the chromatographic column 3 by means of a coupling nut 22. Alternatively, other known suitable sealing means can be employed for providing pressure-tightness between the tube 19 and the evaporator 1. The sample carrier 2 is also provided with a sealing element 23, which in the present embodiment is actually an annular sleeve of deformable material such as rubber enclosed by a metal cup 24 having guides 25 for aligning the tubular element 11 when the needle 8 is inserted into the interior volume of the evaporator 1.

The heretofore described modification of the sample injector according to the invention operates as follows.

Initially, or prior to the sample injection, a flow of carrier gas is continuously conveyed along the conduit 16 to enter the evaporator 1, wherefrom a major portion of the gas tends to enter the chromatographic column 3 and then pass into a detector (not shown, since it has no bearing on the subject of the invention and because its structural arrangement and mode of application are well known to those skilled in the art), whereas a smaller portion (1 to 3 ml/min) of the carrier gas escapes into the atmosphere via the flow constrictor 15 and the tubular element 11. Sample introduction is effected by the syringe 2, and to this end the needle 8 of the hypodermic syringe is inserted into the passageway of the tubular element 11 until the end of the tube 11 extending from the evaporator 1 becomes pressure-tight by virtue of the sealing element 23. The length of the tube 11 is such that at the moment when pressure-tightness is attained the extremity of the needle 8 enters the heated zone of the evaporator 1. The temperature of the heated zone is maintained so as to be sufficient for or in excess of the vaporization point of the mixture being analyzed. Pressure-tightness between the tubular element 11 and the sealing element 23 having been attained, a liquid sample is injected into the heated zone of the evaporator 1 by pressing the mandrin 7 of the hypodermic syringe 2. Upon instantaneous vaporization of the sample in the passageway of the tube 11, an overpressure is produced exceeding some 10 to 20 times the pressure of the carrier gas at the inlet port to the chromatographic column 3. The difference of pressures between the pressure in the passageway of the tube 11 and that at the inlet port to the chromatographic column 3 acts to sweep most of the sample vapours from the passageway of the tube 11 through the constrictor 15 into the extension of the chromatographic column 3, whereafter the sample vapours entrained by the stream of carrier gas are caused to enter the chromatographic column 3 for separation. The amount of sample received by the chromatographic column 3 is determined by the thus produced pressure differential, the resistance value of the constrictor 15 and by the retention time of the syringe needle 8 in the passageway of the tubular element 11. In order to increase the amount of sample transferred into the chromatographic column 3, the injection of the sample is accompanied by an automatic switchover of the shut-off valve 18 from the position shown in FIG. 1 to the position illustrated in FIG. 2, whereby the carrier gas is caused to flow along the by-pass pipe 17 to either escape into the atmosphere or else to enter a buffer vessel (not shown). This position of the valve 18 (FIG. 2) causes a drop in pressure at the inlet port to the column 3, which acts to increase the amount of sample swept from the passageway of the tube 11 through the constrictor 15 into the chromatographic column 3. After the sample has been injected, the syringe needle 8 is extracted from the passageway of the tube 11. This is accompanied by the loss of pressure-tightness of the evaporator 1 followed by the valve 18 automatically switching over from the position shown in FIG. 2 to the position illustrated in FIG. 1. In this position of the valve 18 the flow of carrier gas is caused to be continuously conveyed along the conduit 16 into the evaporator 1, wherefrom a major portion of the flow enters via the tube 19 the chromatographic column 3 for the sample to be separated into constituents, while a smaller portion of the flow is discharged into the atmosphere through the constrictor 15 and the passageway of the tubular element 11, thereby blowing off the sample residues therefrom.

Therefore, the heretofore described modification of the sample injection arrangement is characterized by that introduction of the vapours of the sample under analysis is effected by virtue of a pressure difference between the pressure produced in the passageway of the tubular element 11 during sample vaporization and that at the entrance to the chromatographic column 3. It must be noted that blowing off the structure with the carrier gas escaping into the atmosphere helps to prevent the sample vapours from settling onto the elements of the structure, thus making it possible for a consequent analysis to be free of the elements of the preceding sample, which improves the accuracy of analysis.

Referring now to FIGS. 3 and 4 representing generally two operating positions of another modification of the sample injecting arrangement according to the invention with like elements being designated by like numerals, the embodiment shown in these Figures is a combination of schematic and sectional views and is characterized by that there is a flow constrictor 315 of a constant preselected cross-section interposed between a passageway for evacuating the vapours of the mixture being analyzed defined by the tube 19 and the chromatographic column 3. Further, the conduit 16 for feeding the carrier gas comprises arranged in series a flow governor 26 and a flow divider 27. One outlet line 28 of the flow divider 27 communicates with the passage for evacuating from the evaporator 1 the vapours of the substances under analysis to convey the vapours through the flow constrictor 315 into the chromatographic column 3 and is provided with a shut-off valve 29, such as an electromagnetically controlled valve. Another outlet line 30 of the flow divider 27 communicates with the passageway for evacuating the vapours from the evaporator 1 to the chromatographic column 3. It is arranged downstream of the flow constrictor 315 and is provided with an adjustable flow constrictor 31. Installed at the outlet of the chromatographic column 3 is a detector 32, such as a flame-ionization detector.

The modification of a sample injector according to the invention with reference to FIGS. 3 and 4 operates as follows.

Prior to the injection of a liquid sample (FIG. 3), the flow of carrier gas follows a path from the flow governor 26 to exit the outlet line 30 of the flow divider 27 and is then conveyed continuously via the adjustable flow constrictor 31 into the inlet port of the chromatographic column 3. Most of the flow enters (at the rate of 20 to 30 ml/min) the chromatographic column 3 and then the detector 32. The rest or lesser portion of the flow (1 to 3 ml/min) is conveyed via the flow constrictor 315 to enter the evaporator 1 and is then caused to pass along the tubular element 11 to be released into the atmosphere. With this path of travel of the carrier gas the valve 29 is closed, an optimum flow rate is established in the chromatographic column 3, while a smaller portion of the carrier gas flow acts to backflush or blow off the evaporator 1. Sampling is then effected by means of the syringe 2 serving as a sample carrier, with a predetermined or measured amount of a liquid mixture under analysis thus introduced.

The syringe 2 is provided with a sealing element 23 at the point of contact of the needle 8 with the syringe body 6, the sealing element 23 being in the form of a rubber sleeve slipped onto the needle 8 of the syringe 2 prior to sample injection. The needle 8 of the syringe 2 is then carefully inserted into the passageway of the tubular element 11, this being facilitated by the passageway having a diameter in excess of the outer diameter of the needle 8.

The needle 8 is inserted into the passageway of the tube 11 as far as it goes for the rubber sleeve 23 to completely block the entrance to the passage.

This is accompanied by the valve 29 switching over to the position illustrated in FIG. 4. In this position the valve 29 is open for the flow of the carrier gas escaping from the flow divider 27 to pass along the both outlets 28 and 30 thereof, one path of the carrier gas flow being traceable from the outlet 30 via the adjustable flow constrictor 31 to enter the chromatographic column 3, while another carrier gas flow follows the path from the outlet 28 to enter the evaporator 1, wherefrom it is caused to move along the passageway of the tube 19 and through the constrictor 315 to be also delivered into the column 3. By pressing the mandrin 7 of the hypodermic syringe 2, a liquid sample under analysis is injected into the passageway of the tube 19 located in the heated zone of the evaporator 1. The liquid sample mixture is then caused to vaporize, whereby the vapours are entrained by the stream of carrier gas entering the evaporator 1 from the outlet 28 of the flow divider 27 and conveyed via the flow constrictor 315 to the chromatographic column 3, wherein they are separated at the outlet from the chromatographic column 3 and detected by means of the detector 32. After the sample has been injected followed by separation of the sample mixture into constituents in the chromatographic column 3, the valve 29 closes (FIG. 3) and the needle 8 of the hypodermic syringe can be withdrawn from the passageway of the tubular element 11. The sample injector is thus returned into the mode of operation shown in FIG. 3 for most of the carrier gas flow escaping from the outlet 30 of the flow divider 27 to enter the chromatographic column 3 and a smaller portion thereof to be conveyed via the flow constrictor 315 into the evaporator 1, thereby back flushing or blowing off the passageways of the tubes 19 and 11 to evacuate the sample residues therefrom.

Gaseous samples can be likewise injected by means of the syringe 2, with the rubber sleeve 23 being used in this case as a protective shield blocking a side opening provided in the needle prior to injection.

Figure 5:
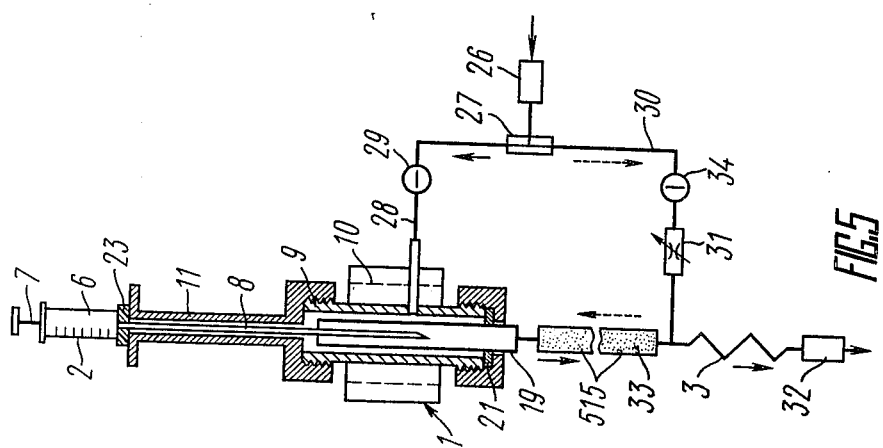
FIG. 5 illustrates, in part schematically and in part sectionally, a modified form of the apparatus according to the invention having a flow constrictor of constant cross-section or simply a flow restrictor in the form of a tube filled with particulate sorbent.

Reference is to be had now to FIG. 5, where there is illustrated, partly schematically and partly sectionally, another modified form of a sample injector according to the invention intended for injecting a fraction of liquid mixture sample composed exclusively of light mixture constituents. The heavier components are not injected into the chromatographic column 3, but are released into the atmosphere via the evaporator 1.

With elements of FIG. 5 similar to those of FIGS. 3 and 4 being designated by the same numerals, the modification represented in FIG. 5 differs from the embodiment of FIGS. 3 and 4 in that a flow restrictor 515 is provided, the restrictor having the form of a tube filled with particulate sorbent 33. A sorbent similar to that filling the chromatographic column 3 or any other suitable sorbent can be employed as the sorbent of the flow restrictor 515. Another feature of the modification under consideration which differs it from the embodiment with reference to FIGS. 3 and 4 resides in that the outlet line 30 extending from the flow divider 27 is provided with an additional controllable shut-off valve 34 operating synchronously with the shut-off valve 29 such that the open position of the valve 29 corresponds to the closed position of the valve 34 and vice versa.

The modification with reference to FIG. 5 operates as follows.

Pressure tightness of the interior volume of the evaporator 1 is attained prior to sample injection by blocking the passageway of the tubular element 11 with the sealing element 23 in the form of a rubber sleeve slipped onto the hollow needle 8 of the syringe 2. This is followed by the injection of a liquid sample into the passageway of the tube 19. Therewith, the valve 29 is open, while the valve 34 is closed. The flow of carrier gas escaping the outlet 28 of the flow divider 27 is conveyed to the evaporator 1 to entrain and carry along the passageway of the tube 19 the vapours of the substances being analyzed and sweep them into the flow restrictor 515. Separation of the sample mixture into two or more fractions or constituents then takes place in the flow restrictor 515 because the tube of the restrictor 515 accommodates the particulate sorbent. After the lighter fraction has been transferred from the flow restrictor 515 to the chromatographic column 3, a switchover of the valves 29 and 34 is effected with the valve 29 assuming a closed position, while the valve 34 opens. The switchover is accompanied by depressurizing the evaporator 1 by removing the needle 8 of the syringe 2 from the passageway of the tubular element 11 and, accordingly, displacing the sealing element 23 away from the entrance to the passageway of the tube 11. In this mode of operation, the flow of carrier gas escaping the outlet line 30 of the flow divider 27 and entering the inlet port of the chromatographic column 3 (the carrier gas flow path is indicated by the dotted arrow) is divided into two streams. One stream tends to enter the chromatographic column 3 to carry therewith the light fraction constituents of the sample mixture being analyzed along the length of the column, wherein they are further separated and detected at the outlet from the column 3 by the detector 32 in the form of separate emission bands. Another stream of the carrier gas enters the flow restrictor 515 to backflush the particulate sorbent 33 blowing off into the atmosphere the heavier fractions not subjected to analysis via the passageways of the tubes 19 and 11. Blowing off the particulate sorbent 33 filling the flow restrictor 515 is continued until all constituents of the light fraction are forced from the chromatographic column 3 into the detector 32 and all the heavier components are evacuated from the flow restrictor 515 into the atmosphere. The heretofore described modification of a sample injector according to the invention affords to prevent the heavier fractions of the mixture under analysis from entering the chromatographic column, thereby reducing the time required for the chromatographic analysis.

Referring now to FIGS. 6 and 7, there is shown, partly schematically and partly sectionally, another embodiment of a sample injector according to the invention intended for injecting into a gas chromatograph samples of vapour phase staying in equilibrium with the liquid or solid substance being analyzed. FIG. 6 illustrates the proposed modification in a position prior to sample injection, while FIG. 7 shows the same during the injection of the vapour phase. The embodiment of FIGS. 6 and 7 differs from the modification shown in FIG. 5 in that the passageway connecting the evaporator 1 with the sample carrier 2 is defined by a hollow needle 35 extending from the evaporator 1, a pointed end 36 of the needle 35 being spaced well away from the evaporator 1. The needle 35 is enclosed in a temperature-controlled housing 37 provided with a heater 38. The pointed end 36 of the hollow needle 35 is fixedly secured to the housing 37 to extend a certain distance therefrom. The sample carrier has the form of an ampoule 39 partially filled with liquid or solid substance 40 under analysis. The upper or neck portion of the ampoule 39 is sealingly blocked by a septum or membrane 41 of self-sealing material, such as silicone rubber, the surface of which is covered by layers of polytetrafluoroethylene. The ampoule 39 is located opposite the pointed end 36 of the hollow needle 35 and secured in a carrier or holder 42 in the form of a temperature-controlled rotatable cartridge accommodating along the circumference thereof a plurality of similar ampoules 39 partially filled with liquid or solid samples to be analyzed. The ampoule 39 is held in the holder 42 capable of axial displacement towards the pointed end 36 of the hollow needle 35 for the pointed end 36 of the needle 35 to pierce the septum 41 of self-sealing material, thereby communicating the interior volume of the ampoule 39 with the evaporator 1. Arranged inside the holder is a heater 43 intended to maintain a preset temperature inside the ampoule 39.

In the preferred embodiment of a sample injector according to the invention as illustrated in FIGS. 6 and 7, the flow constrictor 15 has the form of a capillary tube extending the hollow needle 35, the constrictor being accommodated inside the evaporator 1. The outlet line 28 of the flow divider 27 communicates via the valve 29 with the interior passageway of the hollow needle 35, while the outlet 30 of the flow divider 27 communicates via the valve 34 and the adjustable flow constrictor 31 with the interior volume of the evaporator 1 and the passageway of the tube 19 serving to convey sample vapours into the chromatographic column 3. Alternatively, another modification is possible, wherein the flow constrictor 15 is located outside the evaporator 1 to serve as part of the passageway of the tube 19 for evacuating sample vapours from the evaporator 1 to the chromatographic column 3.

The heretofore described preferred embodiment of a sample injection arrangement according to the invention operates in the following manner.

Prior to sample injection, the holder 42 of the ampoule 39 is in the lowermost position as indicated by broken lines in FIG. 6. At this point of operation the valve 29 is closed and the valve 34 is open. The carrier gas is conveyed from the outlet line 30 of the flow divider 27 into the interior volume of the evaporator 1. Most of the carrier gas flow passes along the passageway of the tube 19 to enter the chromatographic column 3, while a lesser portion thereof (between 10 and 20%) travels along the passageway of the tube 19 to enter the constrictor 15 and the passageway of the hollow needle 35 to be discharged into the atmosphere. This operating position provides that the pointed end 36 of the hollow needle 35 directly overlies the septum 41 of the ampoule 40 to align axially relative to the ampoule 40. On a signal received from a programming unit (not shown), the holder 42 of the ampoule 39 is caused to raise to the uppermost position. The pointed end 36 of the needle 35 pierces the septum 41 of the ampoule 39 to enter the interior of the flask 39 filled with the sample vapours. At this instance the valve 29 opens on receiving a signal from the programming unit, while the valve 34 closes. The carrier gas (FIG. 6) flows along the outlet line 28 of the flow separator 27 to enter the passageway of the needle 35. Travelling along the passageway of the needle 35 and through the flow constrictor 15, the carrier gas enters the chromatographic column 3; the carrier gas also passes along the passageway defined by the interior of the needle 35 and enters the interior volume of the ampoule 39 producing a pressure therein which is essentially equal to the pressure at the inlet to the passageway of the needle 35 (2 to 4 at for the case under consideration). Therewith, the carrier gas tends to be saturated with the vapours of the liquid being analyzed in the interior volume of the ampoule 39. The sample injection is accompanied by the valves 29 and 34 automatically assuming the position indicated in FIG. 7 on receiving a signal from the programming unit, i.e. the valve 34 closed and the valve 29 open. In this position of the valves the value of pressure developed at the inlet port of the chromatographic column 3 is essentially below than that in the interior volume of the ampoule 39, the difference between the pressure values being determined by the pressure differential produced by the adjustable flow constrictor 31; the vapour and gas mixture is then caused to flow from the interior volume of the ampoule 39 to pass along the passageway of the needle 35 and the constrictor 15 and enters the chromatographic column 3. The amount of vapour and gas mixture which enters the column depends on the time of exposure. After a preselected interval of between 5 and 30 sec, the valves 29 and 34 are caused to switch over to the position illustrated in FIG. 6 upon receiving signals from the programming unit; the valve 29 assuming the open position, the valve 34 closing. The stream of carrier gas conveyed from the outlet line 28 of the flow divider 27 into the passageway of the hollow needle 35 acts to prevent the flow of vapour and gas mixture from entering the column 3. After sample injection has been effected, a signal received from the programming unit causes the ampoule holder 42 to be lowered, which is accompanied or followed (with a time lag not over 1 sec) by a switchover of the valves 29 and 34 into the position shown in FIG. 7 (valve 29 closed, valve 34 open). In this position of the valves the carrier gas escapes from the flow divider 27 to pass along the outlet line 30 thereof into the chromatographic column 3 for separation, while a smaller portion (10 to 20%) of the gas flow enters the constrictor 15 to be released via the passageway of the needle 35 into the atmosphere. By virtue of the passageway of the needle 35 being heated to a temperature preventing condensation of the sample mixture vapours, the carrier gas escaping into the atmosphere flushes the residues of the preceding sample away from the passageway of the needle 35. Separation of the constituents of the sample mixture is carried out concurrently with the ampoule holder 42 turning a preset angle for another sample flask 39 to be positioned against the pointed end of the hollow needle 35. Injection of a subsequent sample can thereby be effected in the heretofore described sequence.

Referring now to FIGS. 8 and 9, there is shown, in part schematically and in part sectionally, another preferred embodiment of an arrangement for injecting liquid samples into a gas chromatograph, wherein a micropipette is used as sample carrier; elements of the arrangement similar to those shown in the preceding drawings are indicated by the same numerals. The sample carrier of the arrangement of FIGS. 8 and 9 has the form of a capillary tube 44 fabricated from heat-resistant inert material, such as glass or stainless steel. A boreless or solid end 45 of the capillary 44 is connected with a holder 46, while a lateral bore or drilling 47 immediately adjoins the solid end 45 of the capillary 4. The capillary 44 is further provided with a sealing member 23 in the form of a sleeve of deformable inert material, such as rubber. The holder 46 of the capillary is provided with clamps 49 spring-biased by means of springs 48, the clamps 49 having the form of plates of flexible material, such as steel, provided with crimped hook-like ends 50. The evaporator 1 has a head 51 extending away from the heated area thereof and rigidly connected with the tubular element 11, the passageway of the latter in combination with a passageway in the head 51 serving for insertion of the capillary 44 into the evaporator. The head 51 of the evaporator 1 is further provided with a collar 52 for the crimped ends 50 of the spring-biased clamps 49 to lockingly engage therewith. The collar 52 has on the side thereof facing the capillary being inserted a tapered surface serving as a guide for the hooked ends 50 of the clamps 49 when the capillary 44 is introduced into the passageway of the head 51 of the evaporator 1 and further into the passageway of the tube 11 and when this passageway is pressure sealed through sealing engagement with the sealing element 23. The tapered collar 52 is further provided with grooves 53 (FIG. 9) extending longitudinally therethrough and intended to release the hooked ends 50 of the clamps 49 for depressurizing the evaporator 1 after a sample has been injected into the gas chromatograph. Positioned in the immediate vicinity of the head 52 of the evaporator 1 is a microswitch 54 electrically connected to a control unit 55 for controlling the operation of the shut-off valves 29 and 34, the control unit being generally a time relay. Extending from one of the plates of the spring-biased clamps 49 is a rib 56 cooperating with the microswitch 54 during pressurizing and depressurizing the evaporator 1.

Another feature of this modification as distinguished from the embodiments described heretofore is that connected in parallel to the shut-off valves 29 and 34 are flow constrictors 57 and 58 of constant cross-section, respectively, serving as by-passes of the outlet lines 28 and 30 of the flow divider 27. Connected further to the outlet line 28 of the flow divider 27 is a means 59 to monitor pressure therein, for example a pressure gauge.

The hereinbefore described embodiment operates as follows.

Sample fluid is supplied into the calibrated passage of the capillary 44 by virtue of capillary forces. The movable sealing element 23 blocks the lateral bore or drilling 47 of the capillary 44. Initially, or prior to the injection of a sample into the evaporator 1, the valve 29 is closed, while the valve 34 is open. The carrier gas travels along the outlet line 30 of the flow divider 27 to enter the interior volume of the body 9 of the evaporator, wherefrom most of gas flow (30 to 60 ml/min) is conveyed along the passageway of the tube 19 into the chromatographic column 3, whereas a smaller portion (1 to 5 ml/min) passes through the flow constrictor 15 and the passageway of the tube 11 and head 51 of the evaporator 1 to be discharged into the atmosphere. Therewith, a smaller portion of the flow (1 to 2 ml/min) fed via the flow constrictor 57 acts to blow off a section of the outlet line 28 of the flow divider 27 downstream of the valve 29 to be likewise discharged into the atmosphere.

At the moment of sample injection the capillary tube 44 is inserted into the passageway of the head 51 of the evaporator 1 and is moved as far as it goes. The movable sealing element 23 is thereby pressed against the head 51 to provide sealing engagement therewith blocking the entrance to the passageway of the head 51 of the evaporator 1, while the hooked ends 50 of the spring-biased clamps 49 lock with the collar 52 of the head 51 of the evaporator 1. The rib 56 extending from one of the plates of the clamps 49 is forced into engagement with the microswitch 54 to close the contacts thereof and cause the control unit 55 to issue a signal to the electrically controlled valves 29 and 34 for the valves to be switched into the position as best seen in FIG. 8. In this position of the valves, a major portion of the carrier gas flow travelling along the outlet line 28 of the flow divider 27 enters the passageway of the evaporator head 51 located opposite the lateral bore or drilling 47 of the capillary 44 to sweep a rationed or measured amount of the liquid sample into the passageway of the tube 11 wherein it evaporates and the vapours thereof entrained by the stream of the carrier gas are then carried via the flow constrictor 15 and the passageway of the tube 19 to the chromatographic column 3 for separation and detection at the outlet from the column. The sample injection is accompanied by that a small portion of the flow of carrier gas travels via the flow constrictor 58 of a constant cross-sectional diameter and the adjustable flow constrictor 31 into the interior volume of the body 9 of the evaporator 1 thereby acting to prevent diffusion of the sample vapours into the outlet line 30 of the flow divider 27. Upon completing the injection, which is indicated by a light annunciator (not shown) electrically wired to the control unit 55 governing the operation of the shut-off valves 29 and 34, the holder 46 of the capillary tube 44 is turned, such as counterclockwise as seen best in FIG. 9, until the plates of the clamps 49 are aligned with the grooves 53 of the evaporator head 51. Therewith, the rib 56 of the clamp 49 releases the contacts of the microswitch 54 to switch the valves 29 and 34 into the initial position preceding the sample injection (valve 29 closed; valve 34 open); the capillary tube is then withdrawn from the passageway of the evaporator head 51 thereby depressurizing the evaporator 1. This position of the valves results in that the flow of carrier gas is conveyed from the outlet 30 of the flow divider 27 to enter the evaporator 1 and travels further along the passageway of the tube 19 into the chromatographic column 3, while a smaller portion of the flow (1 to 5 ml/min.) passes via the flow constrictor 15 and the passageways of the tube 11 and the evaporator head 51 to be discharged into the atmosphere, the thus discharged carrier gas backflushing the passageways of the sample residues.

Sample injection can then be recommenced with a subsequent liquid sample to be injected in the heretofore described sequence.

The pressure gauge 59 serves to check the hermeticity of the passageway of the evaporator head 51 after the sealing element 23 has been pressed thereagainst to provide a sealing engagement therewith during the sample injection. If, after the clamps 49 have been locked with the collar 52 of the evaporator head 51, the hand of the pressure gauge 59 changes its position, no adequate pressure-tightness has been attained. To remedy the situation and completely seal the evaporator, position of the head 51 relative to the body 9 of the evaporator 1 must be adjusted, or the sealing element 23 must be replaced.

Figure 10:
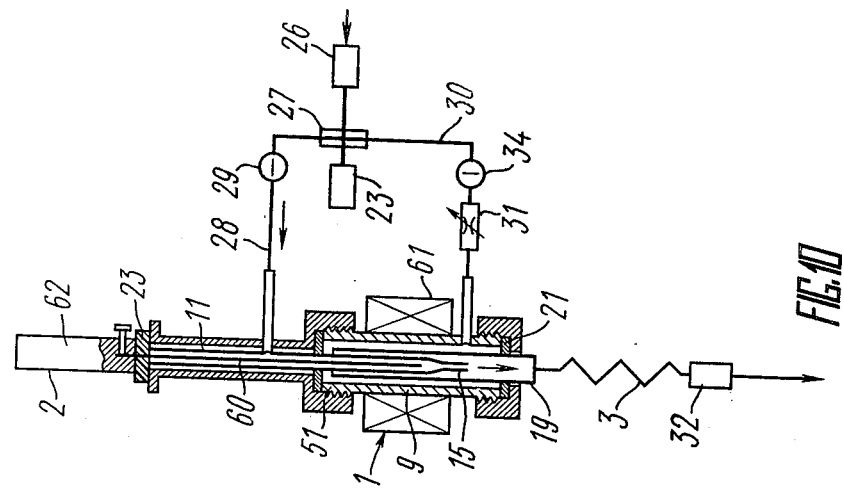
FIG. 10 shows an embodiment of the apparatus according to the invention intended for introducing solid samples.

Another modified form of a sample injector as illustrated in FIG. 10 is intended for injecting solid sample substances. With reference to this FIG. 10, the sample injector comprises the sample carrier 2 fashioned as a rod member 60 of ferromagnetic material, while fitted onto or encompassing the body 9 of the evaporator 1 is an induction coil 61 used instead of heaters in the preceding preferred embodiments.

The ferromagnetic rod 60 is affixed to a holder 62 with the sealing element 23 slipped thereonto. A sample of solid substance is dissolved in a volatile solvent and a measured quantity of the solution is applied, such as by a syringe, to the end surface of the ferromagnetic rod 60. The thus applied sample is then dried in a stream of inert gas or by an infrared radiator such that the vapours of the solvent are swept away leaving at the surface of the rod 60 a thin film of solid substance. The rod 60 is then installed in the evaporator blocking the inlet port of the passage of the tube 11 by means of the sealing element 23. The valve 29 is caused to open for pyrolysis of the solid substance sample to be effected by high frequency current pulses induced by the coil 61; the valve 34 remains closed throughout this operation. In the position of the valves shown in FIG. 10 the entire flow of the carrier gas escaping the flow divider 27 is conveyed along the outlet line 28 into the passageway of the tube 11 to entrain therewith the gaseous and vaporized products of pyrolysis and carry them via the flow constrictor 15 and the passage of the tube 19 into the chromatographic column 3. After the products of pyrolysis have been fed to the chromatographic column 3, the valves 29 and 34 are switched over for the valve 29 to assume a closed position and the valve 34 to open. Therewith, the whole flow of the carrier gas is directed from the flow divider 27 to travel along the outlet line 30 thereof and via the open valve 34, adjustable flow constrictor 31 and then through the passageway of the tube 19 to enter the chromatographic column 3. Thereafter, the rod 60 is withdrawn from the passageway of the tube 11 and a small portion of the carrier gas is caused to escape via the flow constrictor 15 into the atmosphere.

The use of the sample injection arrangement according to the invention will prevent the chromatographic analysis errors usually occurring when septums are employed in the prior art sample injectors, i.e. the herein proposed method and apparatus eliminate the appearance of "ghost peaks" superimposed on the peaks of the components being analyzed. This further helps to prevent the particles of the septum material from penetrating into the interior volume of the evaporator. Another advantage of the sample injection arrangement according to the invention is low manufacturing costs due to that the apparatus is generally made up of standard conventional elements and can be used in conjunction with any known suitable gas chromatograph without substantial changes in its design. Finally, the sample injector according to the invention affords to inject samples of various phases, such as liquid, gaseous, vapour and solid phases.

Disclosed hereinbefore were various embodiments of the invention; however, it shall be apparent to those skilled in the art that such embodiments are subject to various changes and modifications without departing from the spirit and scope of the present invention.

What we claim is:

1. A method of injecting samples into a gas chromatograph, comprising the steps of: communicating a sample carrier in which the sample to be analyzed is contained with an evaporator; pressure-sealing the evaporator with the sample carrier in communication therewith; introducing the sample into the evaporator while the latter is pressure-sealed to form vapours thereof; passing the vapours of the sample to be analyzed from the evaporator through a flow constrictor having a substantially constant cross-section and into a chromatographic column; subsequent to passing the vapours into the chromatographic column, communicating the evaporator with the atmosphere; and while the evaporator is in communication with the atmosphere, passing at least a portion of a carrier gas flow into the evaporator, whereby contaminants are prevented from entering into the chromatographic column with the sample.

2. A method as claimed in claim 1, wherein introduction of the sample into the evaporator is effected by inserting a portion of the sample carrier into the evaporator, the inserted portion having a physical volume substantially equal to or less than the volume of the evaporator; and wherein the sample is passed from the evaporator by causing a flow of carrier gas toward the chromatographic column, vaporizing the sample introduced into the pressure-sealed evaporator to create an overpressure therein, the formed vapours being carried with the carrier gas flow by virtue of the created overpressure into the chromatographic column.

3. A method as claimed in claim 1, wherein the sample vapours are passed from the evaporator to the chromatographic column by causing a flow of carrier gas to be fed into the evaporator after it had been pressure-sealed; and wherein subsequent to passing the vapours into the column, terminating the flow of carrier gas into the evaporator and causing a flow of carrier gas to be directed into an inlet port of the chromatographic column downstream of the flow constrictor.

4. An apparatus for injecting samples into a gas chromatograph provided with an evaporator, said apparatus comprising: a carrier for containing the sample to be analyzed, said carrier having first passageway means for communicating the carrier with the evaporator, a conduit for supplying a carrier gas into the evaporator, second passageway means for evacuating the vapours of the sample from the evaporator into the chromatographic column, a flow constrictor of constant cross-section arranged at the outlet of said first passageway means communicating the sample carrier with the evaporator, said constant cross-section flow constrictor being situated upstream of said second passageway means for evacuating the vapours of the sample from the evaporator into the chromatographic column, a sealing element for hermetically sealing the first passageway means communicating the sample carrier with the evaporator, means for actuating said sealing element so that the same seals said first passageway means only during the period of sample injection, and means for communicating the evaporator with the atmosphere subsequent to said sample injection.

5. An apparatus as claimed in claim 4, wherein the flow constrictor comprises a capillary tube forming an extension of the first passageway means communicating the sample carrier with the evaporator, said capillary tube being positioned inside the evaporator.

6. An apparatus as claimed in claim 4, wherein said flow constrictor is disposed at the outlet of the evaporator to be integral with said second passageway means through which vapours of the sample are evacuated from the evaporator to the chromatographic column.

7. An apparatus as claimed in claim 4, wherein said flow constrictor comprises a tube filled with particulate sorbent.

8. An apparatus as claimed in claim 4, wherein the conduit for feeding the carrier gas is provided with a flow divider, one outlet thereof communicating with said second passageway means for evacuating the vapours from the evaporator to the chromatographic column, said one outlet being positioned prior to said flow constrictor upstream of the flow and having a controllable shut-off valve, and wherein another outlet of the flow divider communicates with said second passageway means for evacuating the vapours after said flow constictor downstream of the flow passing therethrough and wherein said another outlet communicates with an adjustable flow constrictor.

9. An apparatus as claimed in claim 8, further comprising a controllable shut-off valve positioned in the outlet line of the flow divider which is provided with said adjustable flow constrictor.

10. An apparatus as claimed in claim 9, wherein a hollow needle constitutes said first passageway means communicating the sample carrier with the evaporator, said needle having a pointed end extending away from the evaporator and wherein the sample carrier is comprises an ampoule having an upper portion or neck which is sealingly covered by a septum of self-sealing material, the ampoule being mounted for movement toward the pointed end of said hollow needle such that at the moment immediately preceding the introduction of the sample the needle will pierce said septum of self-sealing material to communicate the interior volume of the ampoule with the evaporator.

11. An apparatus as claimed in claim 10, wherein said hollow needle is enclosed by a temperature-controlled housing, the pointed end of the needle extending therefrom.

12. An apparatus as claimed in claim 9, wherein the sample carrier comprises a capillary tube having a hermetically closed end affixed to a holder and further includes a lateral bore adjoining the hermetically closed end, the capillary tube being provided with a movable sealing sleeve of inert deformable material.

13. An apparatus as claimed in claim 12, wherein the holder of said capillary tube is provided with spring-biased clamps in the form of plates of flexible material having crimped hook-like ends, said evaporator having a head member with a collar thereof adapted to lockingly engage with the crimped ends of said plates, the collar of the evaporator head having a tapered surface with grooves longitudinally extending therethrough.

14. An apparatus as claimed in claim 13 further comprising an electrical microswitch positioned proximate to the head member of the evaporator and means for controlling the shut-off valves electrically wired to the microswitch, one of the plates of the spring-biased clamps having a rib cooperating with said microswitch during pressure-sealing the passageway communicating the sample carrier with the evaporator.

15. An apparatus as claimed in claim 9 wherein the sample carrier comprises a rod of ferromagnetic material secured to a holder, the body of the evaporator being provided with an induction coil.

* * * * *